(12) United States Patent
Schuler et al.

(10) Patent No.: US 8,831,738 B2
(45) Date of Patent: *Sep. 9, 2014

(54) SYSTEM AND METHOD TO ELICIT APOPTOSIS IN MALIGNANT TUMOR CELLS FOR MEDICAL TREATMENT

(75) Inventors: Eleanor L. Schuler, Rio Rancho, NM (US); Donald E. Nash, Albuquerque, NM (US); James K. Poliner, Rio Rancho, NM (US)

(73) Assignee: Neuro Code Tech Holdings, LLC, Albuquerque, NM (US)

( * ) Notice: Subject to any disclaimer, the term of this patent is extended or adjusted under 35 U.S.C. 154(b) by 734 days.

This patent is subject to a terminal disclaimer.

(21) Appl. No.: 12/936,778

(22) PCT Filed: Apr. 17, 2009

(86) PCT No.: PCT/US2009/040899
§ 371 (c)(1),
(2), (4) Date: Nov. 1, 2010

(87) PCT Pub. No.: WO2009/151783
PCT Pub. Date: Dec. 17, 2009

(65) Prior Publication Data
US 2011/0270248 A1    Nov. 3, 2011

Related U.S. Application Data

(60) Provisional application No. 61/045,661, filed on Apr. 17, 2008.

(51) Int. Cl.
*A61B 18/12* (2006.01)

(52) U.S. Cl.
USPC ................................ 607/72; 607/2

(58) Field of Classification Search
USPC .......................................... 607/72
See application file for complete search history.

(56) References Cited

U.S. PATENT DOCUMENTS

| | | | |
|---|---|---|---|
| 5,610,136 A | 3/1997 | McMichael |
| 6,575,969 B1 | 6/2003 | Rittman, III et al. |
| 6,937,903 B2 | 8/2005 | Schuler et al. |
| 7,010,356 B2 | 3/2006 | Jog et al. |
| 7,146,210 B2 | 12/2006 | Palti |
| 7,160,239 B2 | 1/2007 | Ichikawa et al. |
| 7,316,913 B2 | 1/2008 | Gerdes et al. |
| 8,315,712 B2 | 11/2012 | Schuler et al. |
| 8,656,930 B2 | 2/2014 | Schuler et al. |

(Continued)

OTHER PUBLICATIONS

Davalos et al.,Tissue ablation with irreversible electroporation, Annals of Biomedical Engineering, vol. 33, No. 2, Feb. 2005.*

(Continued)

*Primary Examiner* — Carl H Layno
*Assistant Examiner* — Jennifer Ghand
(74) *Attorney, Agent, or Firm* — Kermit D. Lopez; Luis M. Ortiz; Ortiz & Lopez, PLLC

(57) ABSTRACT

A method and apparatus for recording, storing and reprogramming the natural electrical signals of cancer cells as found in tumors of humans and animals. A confounding signal is created for retransmission into the cells of a malignant tumor to damage the cell and cause apoptosis. The invention uses ultra low voltage and current to cause apoptosis.

12 Claims, 5 Drawing Sheets

(56) References Cited

U.S. PATENT DOCUMENTS

| | | |
|---|---|---|
| 2001/0051766 A1 | 12/2001 | Gazdzinski |
| 2002/0010491 A1 | 1/2002 | Schoenbach et al. |
| 2003/0170898 A1 | 9/2003 | Gundersen et al. |
| 2004/0072731 A1 | 4/2004 | McMichael |
| 2004/0176804 A1 | 9/2004 | Palti |
| 2005/0171574 A1 | 8/2005 | Rubinsky et al. |
| 2005/0222646 A1* | 10/2005 | Kroll et al. ............ 607/72 |
| 2005/0239047 A1* | 10/2005 | Gimzewski et al. ........ 435/4 |
| 2006/0084942 A1* | 4/2006 | Kim et al. ............ 604/890.1 |
| 2006/0085049 A1 | 4/2006 | Cory et al. |
| 2006/0121590 A1 | 6/2006 | Speerli |
| 2006/0287679 A1 | 12/2006 | Stone |
| 2007/0187840 A1 | 8/2007 | Dell'Acqua-Bellavitis et al. |
| 2008/0187909 A1* | 8/2008 | Dai et al. ............ 435/6 |
| 2009/0232740 A1 | 9/2009 | Rishpon et al. |
| 2010/0016651 A1 | 1/2010 | Sivo |
| 2010/0233021 A1 | 9/2010 | Sliwa et al. |
| 2010/0286689 A1 | 11/2010 | Schuler et al. |
| 2011/0130754 A1 | 6/2011 | Schuler et al. |
| 2011/0270248 A1 | 11/2011 | Schuler et al. |
| 2012/0184800 A1 | 7/2012 | Brighton |
| 2013/0261711 A1 | 10/2013 | Sivo |

OTHER PUBLICATIONS

Hu et al., Simulations of transient membrane behavior in cell subjected to a high-intenisity ultrashort electric pulse, Physical Review E 71,031914(2005).*
Nuccitelli et al., Nanosecond pulsed electric fields cause melanomas to self-destruct, Biochemical and Biophysical Research Communications 343(2006) 351-360.*
Binggeli, "Deficits in Elevating Membrane Potential . . . ", Cancer Research, vol. 45, No. 1, 1985, pp. 235-241.
Marino, "Association between Cell Membrane Potential and Breast Cancer", Tumor Biology, vol. 15, No. 2, 1994, pp. 82-89.
Euler, "Cell proliferation and apoptosis in rat mammary cancer . . . ", Bioelectrochemistry, vol. 62, No. 1, Apr. 2004, pp. 57-65.
Database Biosis, Griffin, "The effects of low-level direct current . . . ", British Journal of Cancer, vol. 69, No. 5, 1994, pp. 875-878.
Extended European Search Report in corresponding EP09763075.0, dated Apr. 26, 2011.
U.S. Appl. No. 12/936,778, filed Nov. 1, 2010, Schuler et al.
U.S. Appl. No. 12/936,791, filed Oct. 28, 2010, Schuler et al.
U.S. Appl. No. 12/334,212, filed Dec. 12, 2008, Schuler et al.
Extended European Search Report in European Application No. EP 09731826.5 dated Dec. 9, 2011.

* cited by examiner

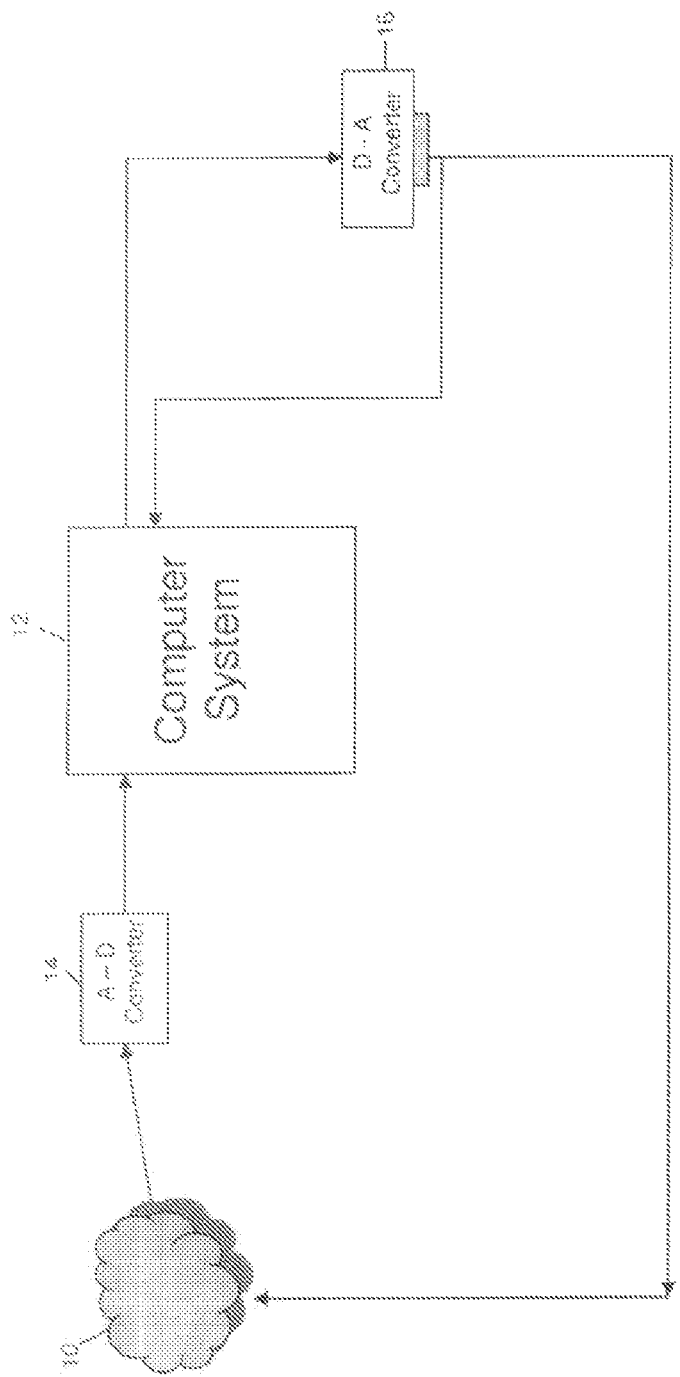
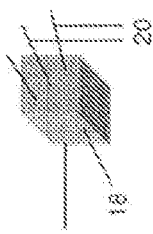
FIG. 5
FIG. 6

SYSTEM AND METHOD TO ELICIT APOPTOSIS IN MALIGNANT TUMOR CELLS FOR MEDICAL TREATMENT

RELATED APPLICATION

This application claims priority to U.S. Provisional Application No. 61/045,661, filed Apr. 17, 2008.

BACKGROUND OF THE INVENTION

The present invention relates to the medical therapy of established cancers on and throughout the animal and human body by causing cell-death by reprogramming intra-cellular communication systems so that they fail by apoptosis. Most particularly, the invention relates to the use of an electronic system that is capable of reaching, detecting and recording intra-cellular analog signals of cancer cells that are organized or formed into islands or clusters of malignancy. Then the cellular signals are reprogrammed for rebroadcast or transmission into the cancer to damage and disable the cell process or cause the cell process to trigger apoptosis (programmed cell death).

This invention is an improvement of the invention disclosed in co-pending International Application No. PCT/US2009/030701, filed Jan. 12, 2009, the disclosure of which is incorporated herein by reference.

All humans and animals are constructed of cells. Cells are the smallest fundamental unit of life. A cell is the smallest living structure capable of performing all of the processes that define life. All cells have electrical and chemical processes. Most cells have also an electrical communication system to operate the cell. The human body is made up of some 100 trillion cells representing perhaps some 300 cell-types. Each cell-type performs a specific function such as operating muscles, glands and vital organs. In addition, nerves, which are made of communicating cells called neurons, provide electrical regulating signals to operate and adjust enormous amounts of functional activities throughout the body to maintain homeostasis (life equilibrium).

Normal cells reproduce by going through a cell cycle that leads to reproduction of similar cells by a process of mitosis which is where a single cell divides and then splits into two daughter cells that are exact replications of the mother cell. Normal cells are limited as to how many times they can reproduce by mitosis. Cancer cells, on the otherhand, reproduce rapidly throughout their life, some at the rate of a complete mitosis every half hour.

A characteristic cell, such as that depicted in FIG. 1, is surrounded by a thin plasma membrane which separates the internal structures and operating organelles from the cells external environment. A portion of that membrane is shown in FIG. 2, in greatly enlarged fashion. It houses and protects the contents of the cell. It consists of a bilayer of phospholipids and various proteins which are attached or embedded.

The plasma membrane is a semipermeable structure that allows passage of nutrients, ions, water and other materials into the cell. It also allows an exit pathway for waste products and for functional two-way passage of many kinds of molecules to adjust cell chemistry. The principal purpose of the cell membrane is to provide a barrier that contains all of the processes and components within the living cell and to simultaneously repel unwanted substances from invading or entering the cell.

Since cells are electrochemical in nature, the plasma membrane is the site for generating the cells' electrical signals for metabolic and other operations and to serve as a means to communicate, relay and receive signals with other cells, especially those of similar type. The nucleus and plasma membrane communicate with electrical signals. The nucleus determines how the cell functions and also determines the architecture of the cell and its contents. The plasma membrane can use electrical signaling to open passageways and ion channels to allow the intake of chemicals as well as the outflow of cellular waste products.

The cell membrane is coated with a relatively thick glycocalyx, which is designed and produced by the cell to protect it and allow it to be recognized. The nucleus has input into the crafting of membrane defensive characteristics. The glycocalyx can produce a negative electric surface charge in cancer cells so as to repel the body immune system.

The cell membrane regulates the flow of materials into and out of the cell. Also it can detect external signals and mediate interactions between other cells. Membrane carbohydrates installed on the outer surface function as cell markers to allow a cell to distinguish itself from other cells.

The plasma membrane contains the sites where the electrical energy is created and the cellular communication signals are formed. These signals are transmitted over the cytoskeleton, which acts like wires, to regulate and trigger metabolic and functional processes within the cell.

The cytoskeleton, a portion of which is shown in enlarged fashion in FIG. 3, maintains the shape of all cells from the inside. It is like a geodesic structure that provides strength and internal areas for electro-chemical timed reactions. Noteworthy is that the cytoskeleton extends with intermediate filaments into other cells and links up with their cytoskeleton (see FIG. 4B) to maintain and form communication links into adjacent cells. The cytoskeleton structure is made up of a network of hollow-microtubules, solid-microfilaments and solid-intermediate filaments. The cytoskeleton is anchored to the plasma membrane and serves as the "wiring" to transmit the cellular communication signals.

The cytoskeleton is made up of actin and myosin which are also found in muscle structures. The cytoskeleton also controls the circulation of the cytosol which is the fluid and semi-fluid that suspends the organelles. Organelles are the functioning entities of the cell that manufacture and distribute cellular products and processes necessary for the cell to live.

Individual cells operate themselves by electrical and chemical processes to maintain life and to perform the function for which a given cell has been constructed. Cancer cells have different electrical signals than normal cells.

Cells generate their electrical energy and communication signals within the plasma membrane. Such membrane also has electrical connections to adjacent cells of the same type to allow uniform information transfer.

As shown in FIGS. 4A-4D, cell communication is both electrical and chemical. Little scientific work has been done to understand electrical cell signals, due largely to the lack of electronic equipment to detect, record and retransmit the tiny cellular waveforms.

The following is useful terminology for cytoplasm and key cellular organelles:

Cytoplasm and Nucleus: The cytoplasm, a fluid which can be rather gel-like, surrounds the nucleus, which is considered an organelle. The nucleus contains the DNA genetic information and hence controls both the activity of the cell and its structural nature. As shown in FIG. 1, the nucleus is spherical and is surrounded by a double membrane, the nuclear membrane and envelope, which is perforated by a significant number of pores that allow the exchange of materials and substances with the cytoplasm.

Mitochondria: An important organelle is the mitochondria which serves as the power station for the cell. They are rod or oval shaped structures functioning as respiration for the cell. A number of mitochondria are scattered within the cytoplasm and move in accordance with its flow, as shown in FIGS. 1 and 3. The product produced as a biological fuel is called adenosine tri-phosphate (ATP). The manufacture of ATP results from the processing of proteins, fats and carbohydrates. The cell communication system supplies the ATP to other organelles that require this bio-fuel to provide processing energy, as needed.

Endoplasmic Reticulum (ER): The ER is a network of membranes that forms channels that criss-crosses the cytoplasm utilizing its tubular and vesicular structures to manufacture various molecules. The system is doted with small granular structures called ribosomes for the synthesis of proteins. Smooth ER makes fat compounds and deactivates certain chemicals like alcohol or detected undesirable chemicals such as pesticides. Rough ER makes and modifies proteins and stores them until notified by the cell communication system to send them to organelles that require the substances. All cells in humans, except erythrocytes (red blood cells), are equipped with endoplasmic reticulum.

Golgi Apparatus: The Golgi apparatus consist of Golgi bodies which are located close to the nucleus and consist of flattened membranes stacked atop one another like a stack of coins. The Golgi apparatus sorts and modifies proteins and fats made by the ER, after which it surrounds and packs them in a membranous vesicle so they can be moved around the cell, as needed. Similarly there is a process to pack up cell waste products for expulsion from the cell via ports in the plasma membrane into the extra cellular spaces.

Lysosomes: Lysosomes are the digestive system for the cell. They contain copious quantities of acids, enzymes and phosphates to break down microbes and other undesirable substances that have entered the cell. They also digest and recycle worn-out organelles to make new cellular structures or parts.

Ribosomes: Ribosomes are tiny spherical organelles distributed around the cell in large numbers to synthesize cell proteins. They also create amino acid chains for protein manufacture. Ribosomes are created within the nucleus at the level of the nucleolus and then released into the cytoplasm.

Cancer occurs in normal cells with birth-defected distorted chromosomes and abnormal genes which lead to the formation of a defective cell which exhibits a severe disorder of mitosis (cell division). The thrust of a cancerized cell is to continuously reproduce by splitting into similar daughter cells uncontrollably.

Cancer cells can reproduce continuously every 30 minutes. When a cell becomes malignant, changes are made in its electrical communication signals.

Once a normal but defective cell becomes cancerized it has a destiny to grow a colony of similar cancer cells without regard to its former normal cell duties and destiny. Defective normal cells that have the potential to become cancerized can be potentially triggered by a number of factors such as cigarette smoke, chemicals, viruses, radiation or other influence. A cancer cell emerges from a normal cell that has undergone a malignant change.

Cancer cells continue to reproduce by splitting (including the nucleus) into two daughter cells which themselves split and grow into adult cancer cells and then split again. This is the splitting process of mitosis that produces daughter-cells which ultimately enlarges into a massive collection of cells forming a tumor. The cells can go to other distant sites by a process called metastasis. Once this metastatic process proceeds the cancer spreads to critical body parts and usually heralds a poor overall outcome for the patient. Cancer cells are unregulated, disorganized and engage in extremely rapid rates of mitosis. When enough cancer cells are made, they form larger tumors which interfere with the duties and nutrition of nearby normal cells.

Cancer does its damage in complex ways that include strangling or distorting organs, blood vessels and nerves as well as working its way into bones, brain and muscles. Groups of cancer cells are connected together and feature an inter-connected electrical communication system internally and between each of the cells within a malignant tumor. Cancer cells perform no function that contributes to the homeostasis (life equilibrium) of the body, in any way.

Cancer cells have developed ways to repel the human body immune system by several means including erecting an electrical shield on the outer surface of the plasma membrane which is produced by the cancer cell, itself. The body's natural immune system is not effective in attacking cancer as it does in attacking invading bacteria or viruses or even malfunctioning cells that have been injured.

Although it might be thought that many cancer cells are not susceptible or capable of undertaking a programmed cell death because of the immortal nature of healthy cancer cells, that is not true. Cancer cells can be destroyed just as normal cells if they lose or experience changes in their cellular communication capability which alters their internal signaling capacity. It may be potentially possible that some healthy cancer cells may initially resist signals to confound their internal communication system. But reprogramming the treatment signals ultimately causes shut-down of the cellular electric system. It is believed that targeted cells are unable to resist the effects of reprogrammed destructive codes that are externally delivered directly into or through the plasma membrane, so the confounding treatment signal reaches the nucleus.

Cancer cells that are born significantly defective or suffer injury to DNA routinely die and are susceptible to being phagocyted and devoured by the immune system. There has been no prior art that attempted to accomplish reprogramming of the intra-cellular communication system of a cancer cell but there have been experiments to punch holes in the cell wall to allow the cytoplasm to drain out and hence kill the cell via a lysis mechanism induced by using 1.5 to 2.5 kilovolts in microsecond pulses. This, however, is a cumbersome cell-by-cell process.

Just as normal cells, cancer cells have a complex cellular wall plasma membrane which allows the passage of desired nutriments and electrolytic ions into the cell and the excretion or expulsion of waste products and certain ions from the cellular interior into the extracellular space. The passage of ions through the cellular membrane generate or create a flow of electric currents through the membrane. The cancer cell membrane is the source of the intra-cellular electrical energy that operates the signaling processes within the cell. The plasma membrane anatomy has evolved as a generator of the electrical energy which is formed into a signaling format that operates a particular cell. The signal characteristics of a cancer cell are different than found in non-malignant cells. When a cancer cell is genetically created from a normal cell the signaling process is altered to allow unlimited reproduction and the erection of a strongly negative electrical charge within the glycocalyx outer wall coating layer on the plasma membrane to protect the cancer cell from the body's own immune system.

The electrical energy generated in the plasma membrane forms signals and transfers them onto close attachments of cytoskeleton filaments. This communication energy moves around the cell via the cytoskeleton acting as both a physical support structure, a series of shelves and hooks to locate cellular processes and to serve as a sort of wire network to allow electrical signals a functional pathway. The malignant cells operations are regulated, switched on or off and combined with chemical areas to initiate electrochemical reactions. The electrical signaling energy presents a format that provides for a communication system not only within a given cell but throughout the entire tumor from one cell to others. This combined electrical flow within and between cells act like an orchestra playing in harmonies via the genetically introduced coded operational and communication signaling system. From the living cells a communication system emerges as a sort of instructional and guidance system which, among other duties, allows for the decision and instructions for selected cells to metastasize to distant sites to establish new colonies of malignant cells. The communication system also is able to signal to nearby blood vessels to generate additional or larger arteries directly into the tumor where upon smaller arterial branches will bud and bring blood with its oxygen to the parts of the tumor cluster that requires such nourishment. This process is called angiogenesis.

First and absolutely, all cells, including malignant ones, have an internal signaling mechanism to coordinate all of their life processes and therefore to remain alive. Intra-cell and cell-to-cell signaling ability exists so that similar cells can work together. An example is the coordinated electric release of adrenalin from all or most of the cells that make up the adrenal gland that sits on top of each kidney in response to a perceived fear event. A release of adrenalin happens when the eyes and/or auditory system have sensed a major danger and transmit a rapid afferent signal to the brainstem and limbic system and most especially the amygdala where fear management is centralized. Once detected as a fearsome danger, an electrical efferent signal races to the adrenal gland and signals for the excretion of adrenalin into the blood stream to bring the entire body to emergency alert status. The body is now ready to fight or to attempt an escape from the danger, all determined by the brain assessment of the potentially fearsome episode. To accomplish all of this no chemical-switching is used except for the actual manufacture and release of the adrenalin chemical stimulant, itself. Everything from sensing danger, to making a decision, to turning on adrenalin and to signal its release into the circulatory blood stream happens virtually instantaneously, all solely by electrical signals. Chemical signaling would have been too slow to respond to an imminent emergency. Because of pre-designated signal inputs and pathways, only the correct cells participated in the emergency. The neighboring kidney plays little part in the emergency. Many cells of the adrenal gland are coordinated to excrete the adrenalin simultaneously so that the correct amount was applied to alert the entire body. That takes successful cellular neuro-signaling communication between a large number of cells, doing it at blinding speed. Digestion is stopped and blood moved into muscles to provide the oxygen for power and speed and the brain's senses are focused into a highly defensive alert and all previous thoughts and activity is shut-down in order to deal with the danger.

An initiating cancer cell starts out as a normal cell but develops a chromosomal and/or a genetic chaos that drives a transformation to malignancy. Prevailing cancer theory blames mutations in important regulatory genes for disturbing the normal controls on cells that are destined to become malignant. Such theory does not give credit to the damaging changes to actual chromosomes that are seen in many cancer cells. The distorted, broken or bent chromosomes unbalance thousands of genes en masse and are sufficient to trigger cellular instability that leads to serious genetic disruption and to account for the transformation of so-called normal cells into malignant ones. The cancer cells retain their electrochemical signaling and operating systems which existed when each cell was a normal cell, but during cancerization a cancer cell rearranges its cellular mechanisms in new ways to disconnect its communication ability from adjacent normal cells and to start rapid reproduction of more cancerous cells which are then connected to communicate only within their own transformed malignant species.

Interestingly, the first cancer cells that are adjacent to normal unaffected cells are sometimes not wired into the rest of the tumor and serve as a barrier separating the rapidly forming tumor from adjacent normal cells. Potentially, these first layers of cells that undergo cancerization are only a demarcation line from malignant to normal and may not have to participate or only partially engage in communications within the cellular command and control signaling system and therefore require less communication capability. Later forming cells do develop the desmosome interconnection communication systems between adjacent cell walls and are fully involved in tumor-wide signaling.

Neither the normal cell nor the malignant cell can live without a functioning electrical signaling mechanism to operate the electro-chemical processes that are shelved in places along the cytoskeleton. The cytoskeleton provides a somewhat flexible geodesic-like framework to maintain cell shape, provides shelf space or hangers for chemical or electrochemical process and allows space for the organelles, nucleus and protein manufacturing elements within the cell. The cytoplasm provides moisture and nutriments and serves as a transport mechanism within the cell. There is a cytoplasmic streaming process that causes directional movement of the liquid or gel-like cytoplasm as a means of local transport for the semi-floating organelles (functional cell components). Likely this allows these floating structures to move about the cytoplasm to connect by some sort of communication link between non-mobile structures located and attached to the cytoskeleton. In addition, contact with the cellular membrane, nucleus and other organelles, becomes possible as they come into various close proximity positions to allow interactive signaling exchange.

The cytoskeleton is composed and constructed of the intermediate filaments which provide the internal structure to maintain cellular shape and make contact into the plasma membrane which allows for distribution of the signals that originate within said membrane. This filamentous structure serves to provide a sort of wiring system for electrical signals to travel to sites of chemical process to coordinate cell-life duties in both normal and cancerous cells. The cytoskeleton intermediate filaments are composed of compounds that are similar to the structures of muscles which have electrical properties. There is a flexibility in the cytoskeleton to take up the effect of movement that occurs throughout all multicellular organisms. The signals traveling via the cytoskeleton most likely initiate and stop the chemical reactions, as required. The electrical signals likely skip and travel along the surface of the filamentous network rather than within the central framework, again on some sort of scheduled or timed basis or in response to some event or instruction. The genetically produced signaling system may be thought of a sort of simplified cellular neuro-system that substitutes for a brain to operate the cell. The nucleus may harbor some sort of instructional pathways that help the cancer cell live and be a member of the overall tumor structure. The nucleus may also provide the signals that release designated cells to undertake metastasis. Access to all systems within the cell by the nucleus is made possible by electrical signal switching and transmissions to rearrange the cell duties. Signaling pathways are altered by inputs and events in what stands in for a sort of cellular intelligence.

Cells become more electro-negative in the course of cancerization, no doubt genetically mediated. Cancer cells seem to reconstruct the cellular membrane access ports to allow the importation of more sodium and sugars than non-cancerous cells of the same size. The electrical potential between the inner and exterior wall layers of the plasma membrane serve as a sort of battery or solid-state generator to supply the power to operate the individual cell including cancer cell. It is believed that during the process of cancerization there is a reprogramming within the communication system for how the cell conducts its business.

The cytoskeleton intermediate filaments are woven or hooked together at their connection points throughout the cell's interior to allow the flexing of the overall cellular structure. Importantly, as shown in FIG. 4B, the intermediate filaments continue protruding through the desmosome which allows a connection to an adjoining cancer cell. This piercing of the cell wall within the desmosome is how signals are sent and received from adjoining cells. There can be several desmosome connections on different aspects of the plasma membrane so as to connect to cells over, under and beside a given cancerous cell, so as to communicate with all. In the alternative, other types of cellular attachment for signal transduction or transmission is likely. Every cell is a unit of life unto itself and has the ability to accomplish some sort of simple primitive reasoning or organized processing as well as communication with its neighboring similar cells.

Beside being barrier cells it is believed that the non-desmosome-connected cells may became the cells that would be released to metastasize, although no one is positive of this. Some cells do not have desmosomes inter-cellular connections but are assembled by tight junctions or intermediate functional mechanisms. It is not known, if cytoskeleton connections touch the point of other types of cellular adhesion as a communication link to adjacent cells or make the transitional connecting in mid-desmosome. There is a likely expectation that all the abutting cancer cells are able to communicate with one another. But how much is communicated between cells may differ. It is suspected that cancer cells that are going to metastasize do prepare themselves to split-away from the tumor cluster. As the cell gets ready to metastasize it gets more compressible. Presumably this is a preparatory part of the process of breaking away from the tumor to travel elsewhere via the lymphatic or vascular system in order to establish a new cancer colony.

It is not known how signals go through to other cells when desmosomes connections are not in attendance. Potentially the other types of cell wall connections do at least allow for the transfer of electrical instructions such as releasing to go and metastasize or to reproduce or even to determine if enough blood supply is available throughout the tumor.

Electrical signals are believed to travel on the surface of the intermediate filaments and reach chemical processes and likely ignite or stimulate a reaction that contributes to reproduction, protein production or metabolic activity. Without electrical activity the cell could not function. Cell biologists know this but have not demonstrated an inclination or capability to address how the electrical component of cells really work. Focus has been on anatomical identification and labeling and in chemical actions and reactions that are present. Such work has been going on for more than one hundred years. The age of electronics with its ever evolving capability and capacity have made it possible to actually trace and study electrical phenomenon in cells.

Cells have electrical zones, part of which concerns the plasma membrane and part of which concerns the nucleus and other cell organelles. The cytoskeleton is connected to the inside of the cell wall and serves as a pathway to distribute electrical communications around the cell. Between the inner and outer cell wall there is an electrical membrane potential that provides clues pointing to the cellular plasma membrane as the source of electrical energy and signal formation. The components within the cell wall function as a sort of solid-state battery or analog electric generator. It can transport ions from the extracellular space into the cell and it can discharge ions and waste as required to maintain the desired properties of the cell. In cancers the charge of the glycocalyx takes on a negative defensive charge to repel the body's immune system during cancerization restructuring.

The question comes to mind as to why have cell biologists concentrated on chemical signaling for the past 100 years? With microscopes, scientists have pursued every corner of the cell, including cancer cells, to study and try to learn what was going on. They have been able to name the anatomical parts of the cell and study at least some of the chemical reactions that occurred on some of the cytoskeleton shelves. But what they have not done is determine anything about the electrical component or the contribution of an electrical signal at any given place within the cell interior. When they did not have full answers they just moved to the chemical reaction explanation, which in itself is amazing when one considers how really small a cancer cell is individually. How the complete communicational cell process fully operates remains, for all practical purposes, a mystery.

Little by little university cell researchers and teaching teams continue to study chemical reaction activity in cellular models. No actual individual cellular communication reactions that involve electricity have been completely demonstrated in the laboratory. Cellular biologists are able to analyze and identify the presence of many cytokine, ions of sodium, potassium, and calcium among others. With the presence of sodium and potassium ions one can bet there is an electrical process going on. Sodium is always involved in sparking signals that are found in all cellular signal processes. The cell is a little tiny unit of life which requires a lot of preparation and various kinds of microscopes to be able to peer into and study. Think of 60 to 400 cells occupying the space taken up by a ball point pen dot and one can imagine how difficult it is to study a single cell. In the beginning the light microscope was used by Robert Hooke during the 17$^{th}$ century to study cells. The electron microscope first introduced by Ernst Ruska in 1933 enabled cells to be explored at up to 50,000 times magnification. The tunneling microscope invented in 1981 by Binnig and Rohrer in IBM's Zurich laboratory has taken the idea of studying a single atom or subatomic particle into the realm of possibility and now opens up the potential for interpreting how chemicals participate with electrical signals in the electrochemical processes to form signals and reactions.

The certain reason as to why scientists have not studied cellular electricity is that there was no proper electronic equipment in existence until the 1990s that could possibly detect, record and allow transmission of these ultra-low power, analog and very fast signals to properly study their contribution to cellular processes. Since the cellular and biochemists have been so invested in the concept of chemical reactions being the communication methodology for cells, they never approached electrical activity as a partner with chemistry to operate cell life. Electrochemical process abound within operating and fast reproducing cells. All cancer cells possess electrical processes to maintain metabolism and plasma membrane operations along with enter and intra cellular communication activities. The present inventors doubt there is any healthy cancer cell that does not have an electrical process working away. Neurons have an electrical signaling process and a cellular electrical process because they are concerned with operation of body systems via the relaying of neuro-codes via nerves. Cancer cells are equipped with internal electrical operating processes that are concerned with protecting, reproducing and the operation of metabolic activity within individual cells as well as internal communication and signaling with adjacent cells. It is also possible that cancer cells are able to communicate to nearby blood vessels to encourage them to extend a new vascular connection to clusters of cancer cells to supply more oxygen and nutrition.

There is an "information minimum" required for life to function in cellular forms that "know" their environmental needs and duties. Cellular systems are completely controlled and regulated with a set of electrical signals that duplicate, or are similar to the natural electrical messages that have been in existence from the beginning of mammalian life. There are signals that require organs to do their job and also signals that report to the brain with a sort of status report as to how well functionality was happening. In fact the brain does coordinate all of the organs simultaneously and confirm that body homeostasis (life equilibrium) is in good order. The cell or cancer cell also has a sort of feed-back mechanism to insure that metabolism, cell transport of food through the plasma membrane, as well as the excretion of cellular waste along with reproduction, metastatic cell release and movement of organelles within the cytoplasm could also be regulated in accord with a sort of grand operational plan. Cells do not have a brain but they do have sensors and feedback mechanisms that provide a simple awareness to the cell and allow for decision processes. The cellular signals exist as sets of instructions and status massages to maintain cellular homeostasis.

SUMMARY OF THE INVENTION

The invention provides a method for treating cancer by causing apoptosis, where the cancer is one of a known species of malignant cells. The method includes the steps of determining the specie of the cancer, and then applying a confounding electrical signal to the cancer by contacting or piercing the plasma membrane of at least one cell of the cancer and applying the confounding electrical signals to cause apoptosis.

In accordance with the preferred form of the invention, the confounding electrical signal is created by determining a resident electrical signal found in the specie of cancer, and then modifying the resident electrical signal to form the confounding electrical signal. The confounding electrical signal is applied with a voltage less than about 2 volts, and with a current less than about 70 microamps. The signal is applied with an imulus, with the imulus preferably comprising a plurality of carbon nanotubes.

Depending on the size of the cancer tumor being treated, multiple applications of the confounding electrical signal may be needed. Therefore, the invention also includes applying the confounding electrical signal to a spaced plurality of cells of the cancer, either simultaneously or at timed intervals.

BRIEF DESCRIPTION OF THE DRAWINGS

The invention is described in greater detail in the following description of examples embodying the best mode of the invention, taken in conjunction with the drawing figures, in which:

FIG. 5 is a schematic illustration of the system according to the invention for determining a resident electrical signal found in cancer, creating a confounding electrical signal and applying the signal to the cancer, and FIG. 6 is a schematic illustration of an imulus treatment tip or probe having a plurality of nanotubes or nanowires.

DESCRIPTION OF EXAMPLES EMBODYING THE BEST MODE OF THE INVENTION

Figure 1:
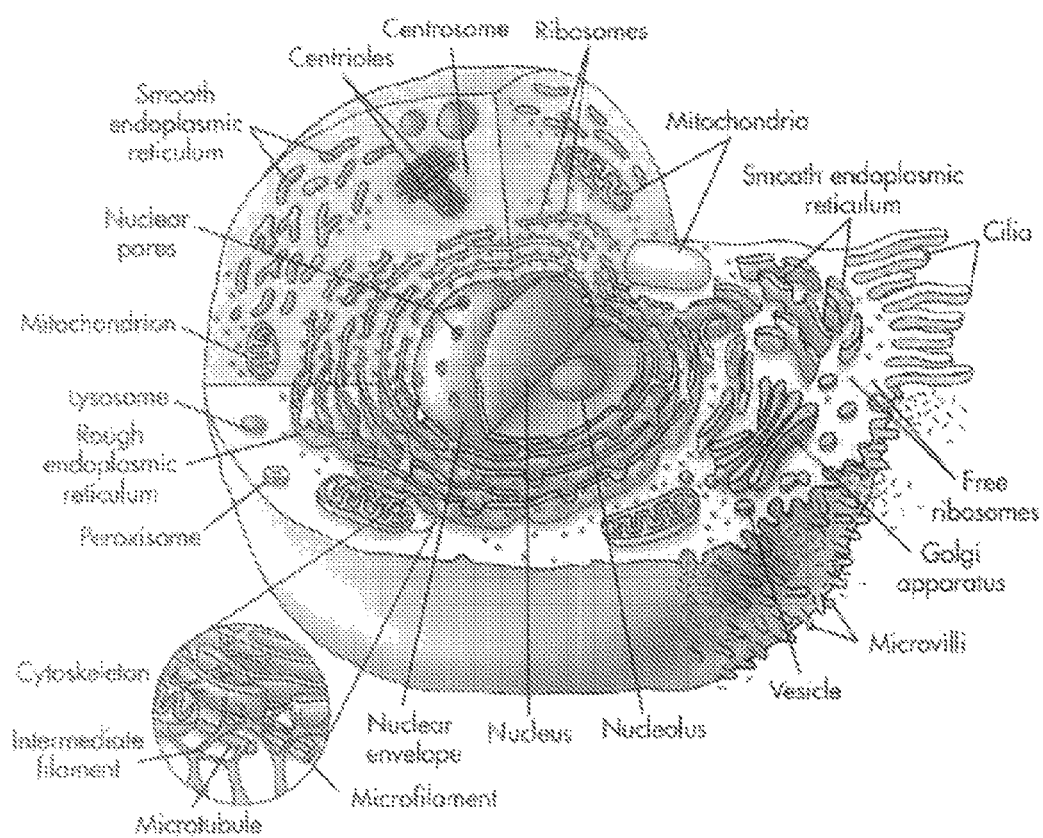
FIG. 1 is a schematic illustration of a characteristic cell.

The present invention provides a system and method for severely disabling cancer cell communication systems that regulate the operation of the most important cellular functions. Cancer cell operating programs and abilities are evolved by genetic development from normal cells through a process of cancerization that readjusts the chemical and electrical systems to take on the duties of a living cancer cell itself from the thrusts of genetic instructions that transforms aberrant normal cells to full-blown malignancies.

The primary aim of the system and method of the invention is to cause cell death that results from disabling the electrical and electrochemical processes that are essential to cellular operations, reproduction and communication.

The invention triggers biologically programmed cell-death which can occur in all cellular bodies when defects or malfunctions develop that impair the future of the injured cell. Once the cellular communication system is damaged and impaired as to function that this will trigger programmable cell death.

All cancer signals are analog in nature since there is no digital signaling capability within human or animal bodies. Therefore the communication processing electronics has to utilize analog to digital converters when recording the cellular signals and then digital to analog converters for transmission or broadcasting reprogrammed treatment signals.

Cancer of the adrenal gland is rare and can affect the adrenal medulla or cortex with something like 400 cases diagnosed per year in the United States. Many adrenal tumors are functioning and produce excess cortisol, aldosterone, estrogens and androgens which impairs many life functions such as glucose tolerance, hypertension, mental status, truncal obesity and fertility disorders. An aggressive surgical approach to adrenal cancer is the preferred therapy with some use of chemo application and radiation. Gaining surgical access to a malignant adrenal cortex or medulla cancers represent a good use for the subject invention to shut-down the signaling system of the targeted malignant cells while sparing the unaffected normal adrenal cells.

The treatment electronic system is designed to detect and record the natural intrinsic signals in and around the cell wall as well as within the interior of the cell itself. The recorded signals are then analyzed and reprogrammed to interfere with the function of a given signal and as a result to trigger apoptosis. The purpose of the invention is to disable, distort, wreck, destroy and to shut-down the electrical process of the cell, without which the cell will die. The treatment electronic system operates with analog to digital converters to record the cellular communication signals because the cells operate in an analog mode. Since computers are generally digital the analog signals recorded from the cell must be transformed into digital format so that the computer processors and software can study and reprogram the signals. Then the digital signals must pass through a digital to analog converter before being transmitted to the cancer cells, as the cells only speak analog.

In the present invention, the ultra-low voltage signals of less than 1 volt at less than 15 microamps are reprogrammed cellular signals which are designed to cause cell apoptosis (programmed cell-death) as medical therapy to rid mammals of cancer within the body. Programmed cell death does not feature or trigger any inflammatory process in the target cell (s). The treatment is designed to damage the communication system in multiple clusters of cells simultaneously. However, depending on the size of the tumor(s) repeat application of the reprogrammed signals may be required for a complete and successful treatment.

This invention makes use of a reprogramming of the above mentioned electrical signal process to be able to alter the shape and electrical properties of the cellular system and to reprogram the system of signals throughout the tumor cellular cluster in a given location of a human or animal body. The most desirable signal alteration would be aimed at causing cell death by how the treatment signals are reshaped to disturb the metabolism, nucleus signaling, protein manufacturing and reproduction mechanisms simultaneously so as to prevent the cell from operating within its normal parameters to accomplish intra-cellular duties.

As discussed above, programmed cell death is called apoptosis. Apoptosis as a bio-medical term indicative that there is a state of natural or induced reprogramming of a cell to enter a suicide mode whereby the cell dies without any inflammatory process, after which the lifeless cell is phagocytized and removed by macrophages of the immune system. Apoptosis does occur in some kinds of cells such as erythrocytes as a method to rid the body of non-performing or defective red blood cells. Cancer cells are thought to not have much opportunity to have preprogrammed cell death because their cell instructions have an immortal ability to continue to reproduce. However, it is known that cancer cells do get programmed if they are born abnormally to commit suicide so not to burden the adjacent well-formed cells already living as part of the growing malignant island or cluster. The cellular program to activate an apoptosis command resides within the nucleus.

Though one can see the anatomy and components of a single cell today it is still impossible to "see" the electrochemical reaction or an individual electrical process going on without a method to record and manipulate its neuro-signal patterns for study. For this the inventors are able to record cancer cell intrinsic signaling properties to serve as a base to reprogram the cancer cell in a manner to cause apoptosis by the use of specialized electronic equipment. The method for recording, storing, reprogramming and re-transmitting communication signals is undertaken directly rather than trying to study signal origination or electrochemical makeup in the cell setting. Recorded signals in and around the plasma membrane and at various areas within the cell interior can be evaluated and altered by reprogramming and then rebroadcast into selected cellular areas to change the overall activity of the cell. Small distinct changes in the signal can be made to focus and refine the desired response directed at confounding and shutting down various processes within the cell. It is expected that as processes close down within a cancer cell there will be a cascade of mal-functional clues leading to collapse of its operations and ultimate failure of the intra-cellular systems.

One of the most important components of the invention includes versions of the imulus contact/treatment device which features carbon nanotube electrode tips embedded in shaped imulus bases with electronic circuitry to carry the signals to the analog processing systems. Because of their high conductivity and strength, carbon nanotubes serve as the ideal contact electrodes for the imulus. The imulus carbon nanotube contact electrodes provide the most delicate structure to deal with the exceedingly small individual cancer cells. These sharp contact electrode points make all the difference in the ability for spearing and piercing the membrane and to get inside the cell for both collecting communication signals and to transmit re-programmed signals through the interconnected tumor communication network that reaches many cancerous cells. The carbon nanotubes may also act as antennas or electrodes in the extremely wet environment of the cell(s) depending on the treatment modality. Each carbon nanotube is connected to a network of wires that can either acquire signals or transmit signals.

Cell signals are delicate, tiny and varied depending on the role they play within the cell. Cell signals are so delicate that a human would not be able to detect them from a single nanotube electrode which was in close contact with a sensitive finger tip. One can expect that the electronic scientific system used to access the cell communication system will be able to present the signals for manipulation or reconfiguring prior to transmitting the intrinsic signals back to the cell(s) to confound the cellular communication apparatus to cause the failure of operational signals required by the cell(s). It is not the power of the signal that is important but rather the shape and configuration of the transmitted treatment signal that is able to elicit important alterations in cellular response. There is little doubt that the intrinsic igniculus signals do control a cancer cell electrical communication process and trigger events that have importance in maintaining cell life. Alterations to those intrinsic igniculus signals will alter cell mechanisms and performance and cripple cancer cellular operation. Since the cells are interconnected with each other the neighboring cancerous cells will be simultaneously damaged by insertion of carbon nanotubes into at least some of the cancer cells and allowing the communication pathways to spread the damaging interclusio input signals to a significant number of adjoining cells with each application. Each contact time will be short, on the order of seconds, to trigger the confounding process that ultimately leads to cellular death.

10,000 carbon nanotubes laying side by side would equal the diameter of a human head hair. They are sharp, as strong as steel and have the conductivity of copper—the perfect electrode. The imulus receives the reprogrammed cellular communication signals and utilizes its pattern of carbon nanotubes as the entry vehicle into the cancer cell cluster or island.

The interface element of the invention is the imulus treatment contact device that features the carbon nanotube electrodes that can pierce the cell wall and record the igniculus intrinsic signals as well as broadcast the treatment signals. There are several formats and shapes for the imulus to allow reaching into different areas of the body and to address different sizes of tumor clusters. There are very small imulus device designs that will better serve the early probing of a cancer site to detect and record the signals associated with each shape, type or species of cancer that is to be treated. In certain treatments the carbon nanotubes will detect and record the signals and electrical activity within or around the plasma membrane. Such signals in the plasma membrane, if they are seriously disturbed, will tend to damage the electrical generating capability of the cellular wall mechanisms. The plasma membrane can act either as a sort of battery or a continuous electrical signal emminator that is linked to the cytoskeleton as a participant in the cell's communication methods.

Figure 2:
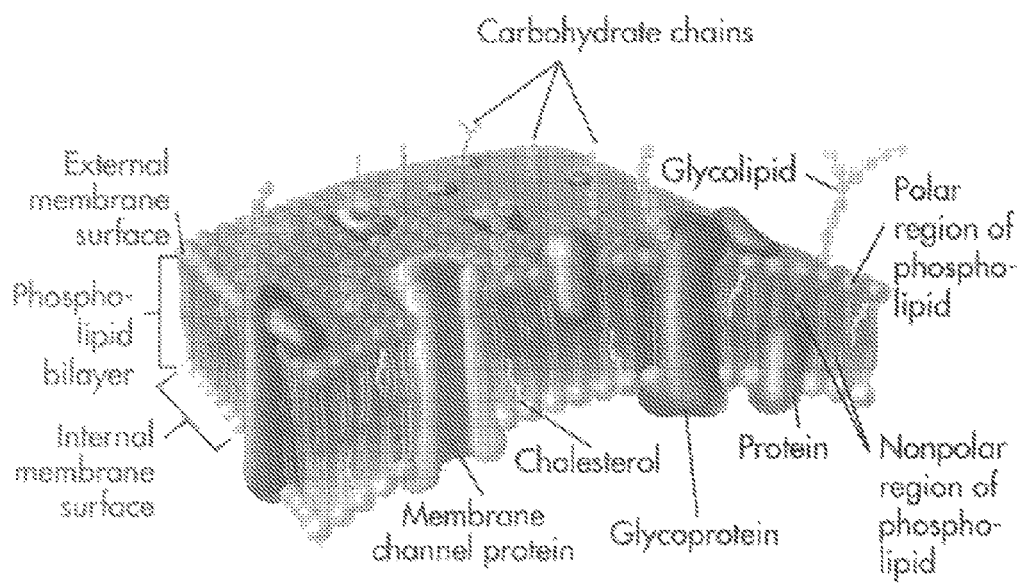
FIG. 2 is a greatly enlarged view of a portion of the plasma membrane of the cell of FIG. 1.
Figure 3:
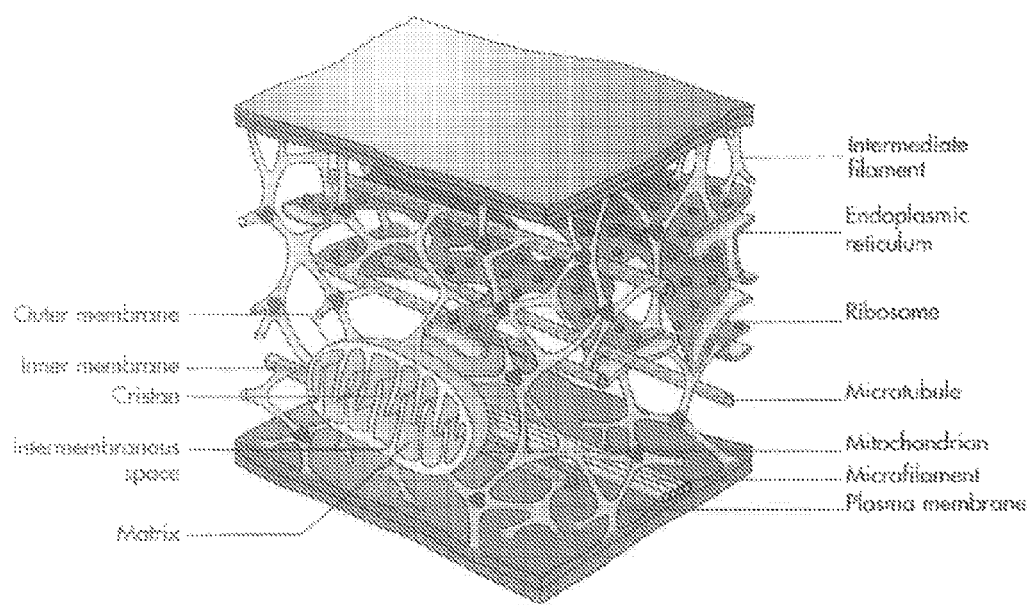
FIG. 3 is a greatly enlarged view of a portion of the cytoskeleton of the cell of FIG. 1.
Figures 4A, 4B, 4C, 4D:
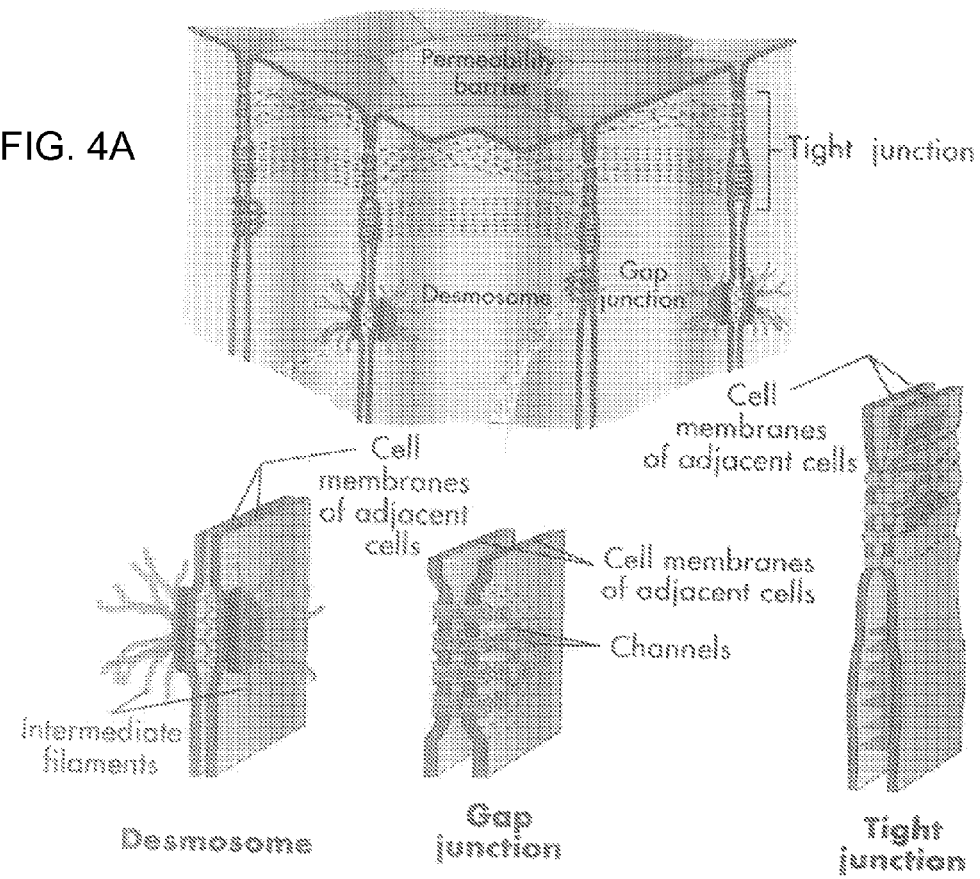
FIG. 4A is a schematic illustration of cell connections of adjacent cells.
FIG. 4B is a schematic illustration of desmosome connections.
FIG. 4C is a schematic illustration of gap junction cell connections.
FIG. 4D is a schematic illustration of tight junction cell connections.

Since the plasma membrane is a source of electrical energy needed by the cell, any damage to the cell wall jeopardizes its participation in the communication process. In fact the plasma membrane, also called the cell membrane or wall, is composed of a phospholipid bilayer with both the external and internal surface membrane and the system of actively working ports (FIG. 2) that transfer nutrients into the cell and expels cellular waste into the extracellular spaces that surround the cells. Such transport can occur by means of diffusion, osmosis or filtration as well as by means of active ion ports which selectively allow the movement of molecule sized ions into and out of the cell. Ion channels determine the electrical and chemical environment within the cell by actively transporting the ingredients required by the cell to accomplish its duties. Some of these ion channels open and close in response to the plasma membrane electrical potential, while other channels are always open and depend on the electrochemical gradients across the membrane. Ligand gated ion channels open and close in response to changes in membrane potential. Whether or not the plasma membrane is considered a generator of electricity or an electro-chemical battery matters little since the important point is that the plasma membrane is the vehicle for providing the electrical energy behind the cellular communication system. The cytoskeleton is the pathway on which the communication system distributes its messages over and to the various cell activities.

Another aspect of the invention is that of interfering with the work of the various organelles within the cell. When the signals are disturbed in such a way that prevents the messages from reaching the various components and activities within the cell it becomes destabilized and malfunctions. Such malfunctions start a cascade of damage that leads to the collapse of both the communication and the intra-cellular operational systems, which will be unable to repair themselves. Adjacent cells will also be disturbed by the appearance of abnormal messages since the cancer cells are linked by a tumor-wide signaling system. As a significant numbers of cells exhibit a cascade of collapsing signaling activity, the tumor is unable to remain organized as a living structure, and apoptosis events begin to emerge followed by irreversible death of the cells of the tumor which are so-affected.

A cancer cell cluster or tumor is illustrated at 10 in FIG. 5. By means of an imulus or other probe, the resident electrical signal or signals of the cancer are then provided to a computer system 12 for storing and processing. Typically, the computer system 12 is digital, and in order to accept the electrical signals from the tumor 10, an analog to digital converter 14 is used. If the computer system 12 employed includes an embedded analog to digital converter, the converter 14 can be omitted.

It is the computer system 12 in which all of the processing, analysis and generation of confounding electrical signals occurs. In order to treat the tumor 10, the confounding electrical signals are applied directly to the tumor 10 via an imulus or probe after conversion to analog state by a digital to analog converter 16.

The technical approach is to initially develop a number of cancer cell resident electrical signals for different species of cancer and perfect reprogrammed confounding type signals. The user then sorts and reprograms the natural signals of the cancer cell and tinkers with the electrical signatures and coding to finally select appropriate treatment electrical signals, also known as confounding electrical signals. This is followed by devising a library/data-base of treatment signals. The collection of treatment signals may be cataloged as to the species of cancer and anatomical location. During treatment of a cancer the first step is to identify the species of cancer and then select the proper confounding signal with which treatment will begin. Once the treatment team knows the species such as carcinoma or sarcoma they select from the computerized library/data-base the most appropriate treatment signal. There are approximately about a total of 200 cancer species in existence. Ultimately the treatment library will be composed of at least as many definitive cancer confounding, interclusio or mortifier signals. Carcinoma species is the most common cancer and likely represents something like 50% of all cancerous tumors arising throughout the body.

Once the cancer cell locations in a patient have been identified, the cancer cellular electrical activity has been recorded and analyzed, and an appropriate response has been determined, the medical staff can develop and initiate a treatment protocol. The protocol will follow established medical procedures with the main objective of applying the proper signals and appropriate electrical energy to the cancerous cells to cause apoptosis. The computer system 12 contains a low voltage and amperage power supply to ensure the correct voltage and amperage is delivered to the cancerous cells. The electrical energy delivered is less than 1 volt and less than 10 millionths of an amp for a pulsed application on the cancer over a few seconds. The treatment may be repeated. The range of electrical treatment may span upwards of 2 volts and 70 micro amps and as low as one-tenth of a volt or possibly even lower at 2 microamps or even lower into the picoamp range. The treatment time may extend up to 4 minutes or more and is repeatable over days if required. The treatment signals in the form of an electrical signal will have a definable shape and be encoded to confound the natural electrical activity found in the cancer cell plasma membrane wall and within the very interior of the cell proper. With the use of the proper code to shut off cellular electricity, the result is apoptosis of the cancer. Cancer death can begin in less than an hour once its metabolic processes are shut-down. Cell death actually may occur in less than 10 minutes as a human brain cells do when blood circulation or electrical signals are turned off. Natural resuscitation of the cancer cell may be possible if the confounding electrical signal treatment is too brief or incomplete. Otherwise irreversible biological decay will set in as long as the cellular process has been severely damaged by the treatment signals. The body immune system is expected to consume the dead or dying cancer as soon as the outer cell membrane negative electric charge is off or markedly diminished. It is the strong negative outer electrical charge of the cancer cell membrane glycocalyx that keeps the immune cells from attacking since they too are negatively charged and would be repelled from one another. Normal cells have outer coat charges that are usually positive and are therefore accessible to the negatively charged immune system cells.

Treatment is done with a small cable of total diameter no more than a wooden match stick. The imulus or treatment contact unit 18, as shown schematically in FIG. 6, is small but may contain up to hundreds or thousands of carbon nanotubes 20. The nanotubes may be hollow or partitioned. In addition they may be coated with a metal deposition, or chemical that interferes with the glycocalyx strong negative electrical charge. The carbon nanotubes equipped imulus 18 will appear under a microscope like a hair brush. Each nano fiber tube is about one-ten-thousandths of a human hair in diameter. The imulus 18 can be used to both record and apply the treatment signal and may be of different sizes to fit the various cancer clusters. The physical approach to the cancer can be guided by fluoroscopy or other visualization apparatus or system to insure that the treatment is applied properly and completely and is directed at the correct target.

The imulus 18 is positioned to make contact with the tumor as the primary junction between the computer system 12 and the malignant cellular tumor 10 which is to be treated. Some modified nano carbon tubes may also act like an antenna and only need to be in close proximity of the malignancy to send in the interclusio or impulses mortifier codes. Insertable links, implantable antennas and contact pads or implacable treatment needles of carbon or metal can be in the arsenal of imulus attachments, among others.

It is preferred that analog computers are used that are as sensitive and able to record the cancer electrical signals as required. As analog computer developments advance they may be more suitable and be the system of choice in destroying cancer cell life. Otherwise the system as illustrated can utilize A-D and D-A converters 14, 16 interfaced with a digital processor in the computer system 12 using appropriate software to control confounding signals.

The main treatment quest consists of locating all of the cancer islands and clusters for treatment. Signals to shut down the cancer must affect every malignant cell at a given site. Communication can travel through portions or layers of tumor cells, traveling from cell to cell. Therefore moving the imulus around the tumor 10 will be necessary to make certain that every cellular communication system present within the malignancy is disabled or destroyed.

While the preferred signal handling system embodiment to destroy cancer cells is a full analog technology, the current state of computer systems is not able to deliver such a scientific computer that would work at the extremely ultra-low voltages and at the speed required to capture and record the natural signals of cancers. Therefore FIG. 5 outlines the requirements for a hybrid system to process cancer treatment codes. The system of the invention uses a hybrid analog/digital computerized system which requires at its entry an A-D converter 14 of high sensitivity to record the exclusively analog cellular signals of cancers. Secondly, the signal has to be transferred into a digital processor in the computer system 12 where it can be stored and reprogrammed to confound the natural cellular signals and control any power supply required.

The computer system 12 includes several components. First, it must have a typical laptop or desktop computer for control, data acquisition, programming and application of treatment. It must allow for storage of ambient and environmental signals as well as potentially interfering biological noise so that the treatment or confounding electrical signals can be as pure as possible. LabVIEW Graphical Software provided by National Instruments Corporation of Austin, Tex. is particularly suitable for handling the graphical aspects of the invention. Insofar as hardware, the National Instruments CompactRIO Control and Acquisition System can be used, or any other similar system of National Instruments or others can be used.

Various features of the invention have been shown and described above. However, it must be understood that what is described herein does not limit but merely illustrates the invention. Various changes can be made to the invention without departing from the spirit thereof or scope of the following claims.

What is claimed is:

1. A method of treating cancer by causing apoptosis, where the cancer is one of known species of malignant cells, comprising the steps of
   a. determining the specie of the cancer, and
   b. applying a confounding electrical signal to the cancer by contacting or piercing the plasma membrane of at least one cell of the cancer and applying the confounding electrical signal to cause apoptosis.

2. The method according to claim 1, in which the confounding electrical signal is applied with a voltage less than about 2 volts.

3. The method according to claim 2, in which the confounding electrical signal is applied with a current less than about 70 micro amps.

4. The method according to claim 2, in which step b includes applying the confounding electrical signal to a spaced plurality of cells of the cancer.

5. The method according to claim 1, in which the confounding electrical signal is applied with a current less than about 70 micro amps.

6. The method according to claim 5, in which step b includes applying the confounding electrical signal to a spaced plurality of cells of the cancer.

7. The method according to claim 1, in which the step of applying is with an imulus.

8. The method of claim 7 wherein said imulus comprise nanotubes that are capable of acting as antennas or electrodes in said at least one cell of the cancer depending a treatment modality.

9. The method of claim 8 wherein at least one nanotube among said nanotubes is connected to a network of wires that acquire signals and/or transmit signals.

10. The method according to dam 7, in which the imulus comprises a plurality of nanotubes.

11. The method according to claim 1, in which step b includes applying the confounding electrical signal to a spaced plurality of cells of the cancer.

12. The method according to claim 11, in which the step of applying is with an imulus.

* * * * *